(12) United States Patent
Wieslander et al.

(10) Patent No.: US 8,367,731 B2
(45) Date of Patent: Feb. 5, 2013

(54) PERITONEAL DIALYSIS FLUID

(75) Inventors: Anders Wieslander, Lund (SE); Ola Carlsson, Lund (SE); Magnus Braide, Göteborg (SE); Per Kjellstrand, Södra Sandby (SE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 571 days.

(21) Appl. No.: 11/921,224

(22) PCT Filed: May 3, 2006

(86) PCT No.: PCT/SE2006/000530
§ 371 (c)(1),
(2), (4) Date: Jun. 23, 2009

(87) PCT Pub. No.: WO2006/130065
PCT Pub. Date: Dec. 7, 2006

(65) Prior Publication Data
US 2009/0306211 A1    Dec. 10, 2009

Related U.S. Application Data

(60) Provisional application No. 60/689,704, filed on Jun. 9, 2005.

(30) Foreign Application Priority Data

May 30, 2005  (SE) ........................ 0501227

(51) Int. Cl.
*A01N 43/00* (2006.01)
*A01N 37/00* (2006.01)
(52) U.S. Cl. ........................ 514/574; 514/183
(58) Field of Classification Search ............ 514/183
See application file for complete search history.

(56) References Cited

U.S. PATENT DOCUMENTS

| | | | | |
|---|---|---|---|---|
| 4,959,175 | A | * | 9/1990 | Yatzidis ........................ 252/364 |
| 6,309,673 | B1 | | 10/2001 | Duponchelle et al. |
| 6,610,206 | B1 | | 8/2003 | Callan et al. |
| 2004/0152666 | A1 | | 8/2004 | Tam et al. |

FOREIGN PATENT DOCUMENTS

| | | |
|---|---|---|
| EP | 0 980 685 | 2/2000 |
| EP | 0 710 483 B1 | 6/2001 |
| JP | 08-164199 | 6/1996 |
| JP | 2000-072658 | 3/2000 |
| JP | 2000-245826 | 9/2000 |
| JP | 2001-181179 | 7/2001 |
| JP | 2001-190662 | 7/2001 |
| JP | 2002-527482 | 8/2002 |
| JP | 2004-331675 A | 11/2004 |
| JP | 2011-511140 | 4/2011 |
| WO | WO 96/01118 | 1/1996 |
| WO | WO 97/06810 | 2/1997 |
| WO | WO 98/29151 | 7/1998 |
| WO | WO 00/23086 | 4/2000 |
| WO | WO 01/21233 A1 | 3/2001 |
| WO | WO 2004/052268 | 6/2004 |
| WO | WO 2005/002599 A1 | 1/2005 |

OTHER PUBLICATIONS

Braide et al., "Citrate supplementation of PD fluid: effects on net ultrafiltration and clearance of small solutes in single dwells," Nephrology Dialysis Transplantation (2009) 24, pp. 286-292.

Sjoland et al., "Intraperitoneal heparin reduces peritoneal permeability and increases ultrafiltration in peritoneal dialysis patients," Nephrology Dialysis Transplantation (2004) 19, pp. 1264-1268.

* cited by examiner

*Primary Examiner* — Sreeni Padmanabhan
*Assistant Examiner* — Timothy E Betton
(74) *Attorney, Agent, or Firm* — Jacobson Holman PLLC

(57) ABSTRACT

The present invention concerns a peritoneal dialysis fluid with enhanced ultrafiltration during the dialysis dwell period. According to the present invention this is achieved by a peritoneal dialysis fluid comprising sodium ions, osmotic agent and a buffer, characterised in that it comprises citrate at a level of 4 to 10 mM in a final solution ready for use.

9 Claims, 1 Drawing Sheet

PERITONEAL DIALYSIS FLUID

CROSS REFERENCE TO RELATED APPLICATIONS

This application is a national phase application based on PCT/SE2006/000530, filed May 3, 2006, the content of which is incorporated herein by reference, and claims the priority of Swedish Patent Application No. 0501227-3, filed May 30, 2005, and the benefit of U.S. Provisional Application No. 60/689,704, filed Jun. 9, 2005, the content of both of which is also incorporated herein by reference.

TECHNICAL FIELD

The present invention concerns a peritoneal dialysis fluid. More particular it relates to a peritoneal dialysis fluid that provides enhanced ultrafiltration during the dialysis dwell period.

BACKGROUND OF THE INVENTION

Peritoneal dialysis is a method for exchanging solutes and water in capillary vessels of a patient's peritoneal membrane with a hypertonic solution, which is infused into the peritoneal cavity. The principle of this method is diffusion of solutes transferred according to the concentration gradient and water migration due to osmotic differences over the peritoneal membrane. This method has many advantages, e.g. that no special apparatus is commonly required, it gives less influence on the hemodynamics because extracorporeal circulation of the patient's blood is not necessary, and further the peritoneal dialysis is a continuous treatment and therefore more similar to the function of the kidneys.

Peritoneal dialysis is usually classified as continuous ambulatory peritoneal dialysis (CAPD), intermittent peritoneal dialysis (IPD), continuous cyclic peritoneal dialysis (CCPD) or automated peritoneal dialysis (APD).

In CAPD a catheter is permanently implanted in the abdominal wall of the patient and about 1.5 to 2.5 l of a dialysis fluid is normally introduced via the catheter into the peritoneal cavity. The peritoneal cavity is flooded with this fluid, left for an appropriate lapse of time and then drained. Removal of solutes and water takes place across the peritoneal membrane, which acts as a semi-permeable membrane.

The dialysis fluid normally used for peritoneal dialysis is an aqueous solution comprising an osmotic agent such as glucose and the like, electrolytes such as sodium, potassium, calcium, magnesium, and organic acid salts such as sodium lactate, sodium bicarbonate, and/or sodium pyruvate. The components of these peritoneal dialysis fluids are selected to control the levels of electrolytes or the acid-base equilibrium, to remove waste materials and to efficiently carry out ultrafiltration in order to keep the fluid balance correctly within the patient.

Inadequate fluid and solute transport is one very important reason for drop out from the peritoneal dialysis treatment. Continuous exposure of the peritoneal membrane to non-biocompatible solutions could cause an inflammation in the peritoneal membrane, and this might be one cause for the impaired function of the peritoneal membrane. This inflammatory reaction may involve complement and coagulation cascade and it has been demonstrated in clinical studies that complement and coagulation systems are activated in PD patients. The addition of heparin, which is known to inhibit complement and coagulation cascade, has been reported to decrease angiogenesis and also to increase ultrafiltration. An increased ultrafiltration will lead to an improved fluid and solute removal and patients can remain on PD for a longer period of time.

However, heparin and derivates thereof are difficult to use in PD fluids because the PD fluids are sterilised at high temperatures and heparin and the derivates thereof is not stable at such high temperatures. There are studies in which the patients are told to inject the substance, such as heparin, into the bag just before use, see e.g. EPO710483, but this is a complicated procedure for the patient.

In WO 01/21233 a dialysis fluid is disclosed comprising 0.8-6.67 mM citrate, preferably 0.8-5 mM and most preferably 1-3.33 mM citrate, 1.75-2.5 mM calcium ions, 0.5-1 mM magnesium ions and less than 60 g/L glucose. The advantages according to WO 01/21233 is that in a hemodialysis treatment a local anticoagulation is provided, which enhances blood flow through the artificial dialysis membrane, enhances the "dialysis dose", keeps the artificial dialysis membrane cleaner, and give rise to a higher clearance of molecules with middle size (about 12 000 D).

In WO 00/23086 a dialysis fluid concentrate is disclosed, and one embodiment is a PD fluid, which, when ready for use, preferably comprises 0.17-2 mM citrate. Here the citrate is added to ensure proper pH within the dialysis fluid, and the preferred range to meet this in a PD solution is 0.17-2 mM citrate in the final PD fluid ready for use.

In U.S. Pat. No. 6,610,206 a dialysis fluid concentrate is disclosed, and one embodiment is a PD fluid, which, when ready for use, comprises 0.5-6 mEq/L citrate, which equals 0.17-2 mM citrate.

In EP 1 124 567 a dialysis fluid concentrate is disclosed, and one embodiment is a PD fluid, which, when ready for use, comprises 0.17-2 mM citrate.

In WO 98/29151 a dialysis fluid is disclosed, which is intended for use as a dialysis fluid for hemodialysis and which comprises 1-15 mM citrate. Also here, as in WO 01/21233, the citrate is added as a local anticoagulant within the artificial dialysis membrane.

SUMMARY OF THE INVENTION

One object of the present invention is to provide a PD fluid that provides increased ultrafiltration without a last minute addition of a substance within the PD fluid.

According to the present invention this is achieved by a peritoneal dialysis fluid comprising sodium ions, osmotic agent, and a buffer, characterised in that it comprises citrate at a level of 4 to 10 mM in a final solution ready for use. In one embodiment the peritoneal dialysis fluid comprises citrate in a concentration of 7-8 mM in the final solution.

In another embodiment of the present invention the peritoneal dialysis fluid comprises 1-10% by weight of an osmotic agent, 90-140 mM sodium ions, and 0.0-1.75 mM calcium ions in the final solution.

In another embodiment of the invention the peritoneal dialysis fluid comprises 0.0-0.75 mM magnesium ions in the final solution.

In another embodiment of the invention the peritoneal dialysis fluid the osmotic agent is chosen from the group comprising glucose and glucose like compounds, polymers thereof, amino sugars, essential and non-essential amino acids, proteins like albumin, and N-acetyl glucose amine (NAG).

In even another embodiment of the invention the peritoneal dialysis fluid comprises, as a buffer, lactate in a concentration of 5-28 mM in the final solution, and in another embodiment of the present invention the peritoneal dialysis fluid comprises, as a buffer, bicarbonate in a concentration of 5-28 mM in the final solution.

In another embodiment of the present invention the peritoneal dialysis fluid comprises 1.5-4% by weight of glucose as the osmotic agent in the final solution. In a further embodiment the peritoneal dialysis fluid comprises 5-10% by weight of glucose polymer as the osmotic agent in the final solution, and in even a further embodiment the peritoneal dialysis fluid comprises 1.5-4% by weight of N-acetyl glucose amine (NAG) as the osmotic agent in the final solution.

The citrate included in the PD fluid according to the present invention could be added as citric acid and salts thereof, including but not limited to sodium, calcium, magnesium, and potassium salts thereof.

The inventors to the present invention have been able to prove in an in vivo test and in vitro tests that by adding citrate to a PD fluid the ultrafiltration during a dwell is enhanced. This is probably due to the fact that citrate complex binds calcium ions, and as calcium ions are one of the components of the complement cascade, the activation of the complement cascade is impeded and by this inflammation within the peritoneal membrane is decreased. By keeping the inflammation low, the vasodilatation due to inflammation is reduced, and thus the osmotic agent, e.g. glucose, has a less tendency to become absorbed into the blood vessels. As the osmotic agent is kept longer in the peritoneal cavity, the osmotic force, which pulls the fluid out from the patient, is effective for a longer period of time. When the dilation of the vessels are minimized the diffusion of solutes also becomes less efficient, but this is compensated by the enhanced convective transport, and the total clearance is enhanced after a 4-hour dwell period.

Additional objects, features, advantages and preferred embodiments of the present invention will become apparent from the following detailed description when taken in conjunction with the enclosed patent claims.

DEFINITIONS

The term "osmotic agent" is intended to mean a substance in a fluid that causes an osmotic force to pull fluid from the patient to the dialysis fluid if present in a sufficiently high concentration. Accordingly, fluid is transported over the peritoneal membrane into the PD fluid. Osmotic agents, which could be used in the PD fluid according to the invention, includes but is not limited to the following substances: glucose and glucose like compounds, polymers thereof including amino sugars, essential and non-essential amino acids, proteins like albumin, and N-acetyl glucose amine (NAG).

The term "single solution" is intended to mean one solution kept isolated from other solutions up until use.

The term "a final solution" is intended to mean the solution which includes the required different single solutions and which is ready for use.

The term "multi-compartment bag" is intended to mean bag divided into more than one compartment and that the content in the different compartments could and in some cases should be brought together and mixed before use.

BRIEF DESCRIPTION OF THE DRAWING(S)

DETAILED DESCRIPTION OF THE INVENTION

The inventors to the present invention proved the positive effect of the addition of 4-10 mM citrate in the following in vitro tests and in vivo test.

Figure 1:
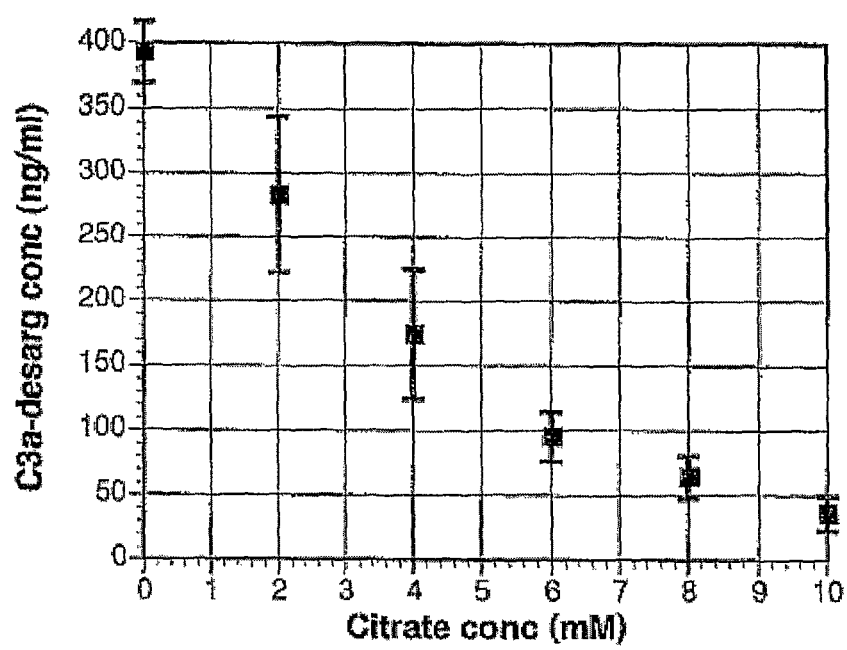
FIG. 1 shows an in vitro "dose and respond"-curve for the inhibition of the complement activation by use of a PD fluid comprising citrate.

The complement activation was determined from the concentration of C3a-desarg measured by ELISA (rat C3adesARG ELISA #CL89160K; Cedarlane Laboratories Ltd., Hornby, Ontario, Canada). The C3a-desarg levels were expressed as concentrations. Venous blood was used and introduced in a lepirudin treated 5 cc syringe (50 µl lepirudin (5 mg/ml)+70 µl PBS in the syringe and needle). 0.4 ml was transferred to a 3 cc tube with 1.5 ml PD fluid with citrate additions of 0, 2, 4, 6, 8, and 10 mM, respectively, (i.e. 0, 12, 24, 36, 48, 60 µl of a citrate solution with the citrate concentration of 250 mM). Thereafter the samples were spun to remove the blood cells. 1 ml of the supernatant was transferred to a new tube, 20 µl Zymosan (20 mg/ml) was added and the tube. Thereafter EDTA was added to a final concentration of 15 mM, the Zymosan was spun down, and samples of the supernatant were used for the ELISA measurement referred to above. The result is shown in FIG. 1. As evident from FIG. 1, the C3a-desarg concentration decreased with increasing citrate concentration. However, the upper limit of citrate, which could be present in a PD fluid, is limited by the total amount of buffer solution within the PD fluid. The amount of added citrate influence the total amount of buffer in the PD fluid since citrate also give rise to a buffer effect. Thus, the buffer used in the PD fluid has to be decreased equal to the equivalent amount of added citrate. The total amount of buffer is usually about 35-40 mEq/L within a PD fluid, and 4 mM citrate equals 12 mEq/L buffer and 10 mM citrate equals 30 mEq/L. Accordingly, the additional added buffer will be about 5 to 28 mEq/L.

Further, the upper limit of added citrate is also limited by the fact that the inhibition of the complement cascade should be limited to the complement cascade within the peritoneum and the walls thereof, and not give rise to a systemic complement cascade inhibition.

Figure 2:
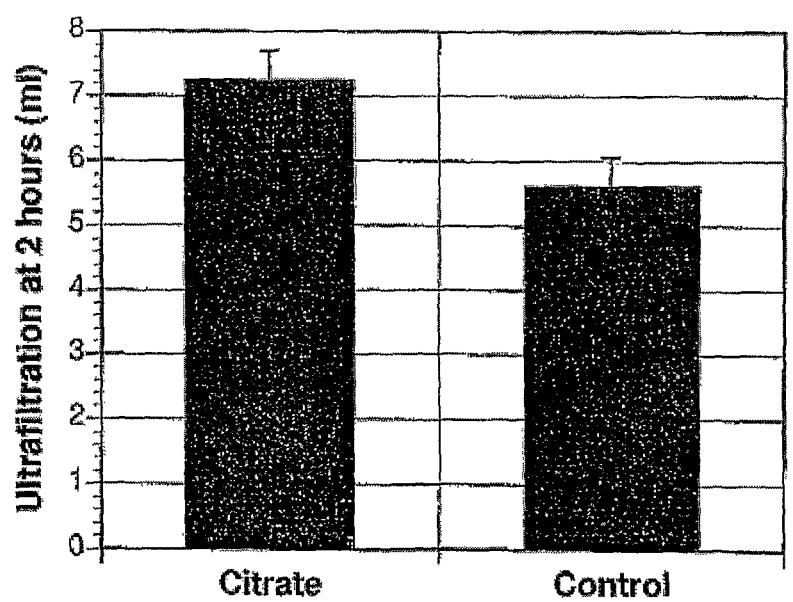
FIG. 2 shows the effect of a PD fluid comprising citrate of the ultrafiltration at 2 hours after infusion of the PD fluid in an in vivo test module.

The lower limit of the citrate concentration is evident from FIG. 1, where a reasonable inhibited complement cascade is provided with a citrate concentration of at least 4 mM. The ultrafiltration volume was determined with the aid of a fluorescence labelled albumin. This was used as volume marker according to a recently developed technique, in which Texas Red® labelled bovine serum albumin (TR-BSA) has been used as a tracer for determinations of plasma volume. The fluorescence characteristics of TR-BSA (Molecular Probes, Eugene, Oreg., USA) solved in fresh and used PD fluid were evaluated, showing a linear relationship between fluorescence (excitation at 570 nm and emission at 615 nm) and concentration in the range of 0-20 µg/ml. By adding 1 mg/ml of unlabeled bovine serum albumin, a small difference in baseline fluorescence between the fresh and the used PD fluid was eliminated. Calibration against $^{125}$I human serum albumin showed very good correlation between the two techniques (correlation coefficient=0.994). In the present tests, 100 µg Texas Red® labelled bovine serum albumin and 1 mg unlabeled BSA was added to 20 ml PD fluid and intraperitoneal volumes were determined from the dilution calculated from fluorescence values of cell-free samples. The intraperitoneal volumes obtained from measurements of Texas Red® albumin after PD fluid exposure increased when citrate was added to the PD fluid, see FIG. 2. The citrate concentration used in the test of FIG. 2 was 10 mM.

Apart from providing the enhanced ultrafiltration, citrate in a PD fluid further has the advantage of "hiding" calcium and/or magnesium within the PD fluid from interaction with bicarbonate, as citrate complex binds calcium and magnesium ions. With this "hiding", bicarbonate is unable to react with calcium and magnesium in order to precipitate as calcium carbonate and magnesium carbonate, respectively.

The peritoneal dialysis (PD) solution according to the present invention could further be arranged in different ways up until use. The PD fluid could be contained in a one compartment bag as a final solution and be ready for use directly. The pH of the PD fluid as a final solution, which is ready for use, would have a pH of 5.5-7.0.

In another embodiment of the present invention the PD fluid is contained as single solutions contained separately in different bags or in different compartments of a multi-compartment bag. Just before use, the content in the different compartments is mixed into a final solution, which then could be used to infuse into the peritoneal cavity. The reason for dividing the PD fluid could be that two different constituent not should be within one solution during sterilisation and storage due to reactions, precipitation, degradation and so on. One example of two components that preferably should be kept apart is calcium ions and bicarbonate, and magnesium ions and bicarbonate, which otherwise would react with each other and form precipitation of calcium carbonate and magnesium carbonate, respectively.

Further, glucose should preferably be kept in a higher concentration, preferably more than 20% by weight, and also at a lower pH, preferably at a pH within the range of 1.8-2.6, during sterilisation and storage. This is the same for glucose polymers. For NAG, the pH should preferably be kept within the range of 2.5-3.5 during sterilisation and storage. To be able to fulfil this the PD fluid have to be divided into two single solutions just up until use. Otherwise glucose will degrade into toxic glucose degradation products, which is detrimental to the peritoneal membrane.

Accordingly, PD fluids containing these components preferably should be kept divided into at least two single solutions during sterilisation and storage, and should then be mixed just before use.

In another embodiment of the present invention the PD fluids is contained as three single solutions up until use. The reasons for the three different compartments is then to be able to facilitate the possibility for the patient to, by themselves, decide which concentration of osmotic agent is needed for that particular dwell period. By providing a bag with three compartment, with two compartments with single solutions of glucose at different concentrations and/or volumes (could also include some additional electrolyte and so on) and one larger compartment with a single solution including the buffer and the rest of the electrolyte composition, the PD patient could make different combinations and get final solutions with different concentrations of osmotic agent. If the single solution in the large compartment is combined with the first of the two glucose single solutions, a first glucose concentration is obtained. If the single solution in the large compartment is combined with the second of the two glucose single solutions, a second glucose concentration is obtained. Finally the PD patient could also combine all of the three compartments and thereby get a third glucose concentration. Also here, if glucose or glucose polymers is used, these should be kept in a concentration of at least 20% by weight, and preferably also at a pH within the range of 1.8-2.6 during storage and sterilisation.

Concerning bicarbonate, this composition in it selves may also create problems. Firstly, as disclosed above, bicarbonate easily precipitates with one of the essential elements in dialysis fluids, viz. calcium, to form calcium carbonate, and secondly bicarbonate solutions emit carbon dioxide and are thus unstable.

The problem with the precipitation could be cured by separating bicarbonate and calcium in two different containers/compartments in two different single solutions during sterilization and storage, and then mix these single solutions just before use.

However, the problem with the emitted carbon dioxide still remains.

If carbon dioxide leaves the bicarbonate solution, the result is an increase of pH up to 9-10.5 depending on the original bicarbonate concentration. According to prior art, this problem is solved either by use of a gas barrier for carbon dioxide or by allowing the bicarbonate to slowly equilibrate with the atmosphere, which is disclosed in U.S. Pat. No. 6,309,673. A further, way to solve this is by using a defined combination of bicarbonate and carbonate in such proportions that the partial pressure of carbon dioxide, $CO_2$, in this single solution is in the same order of magnitude as the partial pressure of carbon dioxide, $CO_{21}$ of the atmosphere. When using such a single solution addition of an additional single solution is required before use, which additional single solution comprises an acid and has a pH of 1.0-1.5.

EXAMPLES

By way of example, and not limitation, the following examples identify a variety of solutions made pursuant to embodiments of the present invention.

In all the following examples tri-sodium citrate has been used but it is possible to use any form of salt of citric acid or citric acid it self. However, the amount of sodium chloride, magnesium chloride, or calcium chloride has to be adjusted to get the desired final composition of the fluid if another salt of citric acid than trisodium citrate is used.

One compartment Bags:

|  | Example 1 | Example 2 | Example 3 |
| --- | --- | --- | --- |
| Volume (l) | 2.05 | 2.05 | 2.05 |
| Glucose (g/l) | 15-40 | 0.0 | 15-40 |
| Polyglucose (g/l) | 0.0 | 70.0 | 0.0 |
| Na$^+$ (mM) | 132.0 | 132.0 | 132.0 |
| Ca$^{2+}$ (mM) | 1.75 | 1.75 | 0.0 |
| Mg$^{2+}$ (mM) | 0.25 | 0.25 | 0.25 |
| Cl$^-$ (mM) | 96.0 | 96.0 | 99.5 |
| Lactate (mM) | 25.0 | 25.0 | 0.0 |
| Bicarbonate (mM) | 0.0 | 0.0 | 25.0 |
| Citrate (mM) | 5.0 | 5.0 | 5.0 |

One compartment Bags:

|  | Example 4 | Example 5 | Example 6 |
| --- | --- | --- | --- |
| Volume (l) | 2.05 | 2.05 | 2.05 |
| Glucose (g/l) | 15-40 | 0.0 | 15-40 |
| Polyglucose (g/l) | 0.0 | 70.0 | 0.0 |
| Na$^+$ (mM) | 132.0 | 132.0 | 132.0 |
| Ca$^{2+}$ (mM) | 1.00 | 1.75 | 1.00 |
| Mg$^{2+}$ (mM) | 0.25 | 0.25 | 0.25 |
| Cl$^-$ (mM) | 97.5 | 101.0 | 94.5 |
| Lactate (mM) | 0.0 | 0.0 | 5.0 |

-continued

|  | Example 4 | Example 5 | Example 6 |
|---|---|---|---|
| Bicarbonate (mM) | 25.0 | 5.0 | 5.0 |
| Citrate (mM) | 5.0 | 10.0 | 10.0 |

Two-compartment Bags:
Compartment 1:

| Example | 7 | 8 | 9 | 10 |
|---|---|---|---|---|
| Volume (l) | 0.100 | 0.100 | 0.100 | 0.100 |
| Glucose (g/l) | 500 | 500 | 500 | 500 |
| $Na^+$ (mM) | 92.0 | 92.0 | 92.0 | 92.0 |
| $Ca^{2+}$ (mM) | 0.0 | 35.0 | 10.0 | 10.0 |
| $Cl^-$ (mM) | 92.0 | 162.0 | 112.0 | 112.0 |
| Citrate | 0.0 | 0.0 | 0.0 | 0.0 |

Compartment 2:

| Example | 7 | 8 | 9 | 10 |
|---|---|---|---|---|
| Volume (l) | 1.900 | 1.900 | 1.900 | 1.900 |
| $Na^+$ (mM) | 134.1 | 134.1 | 134.1 | 97.3 |
| $Ca^{2+}$ (mM) | 0.0 | 0.0 | 0.53 | 0.53 |
| $Cl^-$ (mM) | 96.2 | 92.5 | 93.6 | 98.9 |
| Bicarbonate (mM) | 0.0 | 26.3 | 26.3 | 5.26 |
| Lactate (mM) | 26.3 | 0.0 | 0.0 | 0.0 |
| Citrate (mM) | 5.26 | 5.26 | 5.26 | 10.52 |

Solution, mixed and ready for use:

| Example | 7 | 8 | 9 | 10 |
|---|---|---|---|---|
| Volume (l) | 2.0 | 2.0 | 2.0 | 2.0 |
| Glucose (g/l) | 25.0 | 25.0 | 25.0 | 25.0 |
| $Na^+$ (mM) | 132.0 | 132.0 | 132.0 | 132.0 |
| $Cl^-$ (mM) | 71.0 | 96.0 | 94.5 | 99.5 |
| Citrate (mM) | 5.0 | 5.0 | 5.0 | 10.0 |
| Bicarbonate (mM) | 0.0 | 25.0 | 25.0 | 5.0 |
| Lactate (mM) | 25.0 | 0.0 | 0.0 | 0.0 |
| $Mg^{2+}$ (mM) | 0.25 | 0.25 | 0.25 | 0.25 |
| $Ca^{2+}$ (mM) | 1.75 | 1.75 | 1.00 | 1.00 |

To obtain 15 or 40 g/l glucose, 60 and 160 ml of the solution in the first compartment has to be used. The electrolytes and the volume of the second compartment have to be adjusted accordingly.

Three-compartment Bags:
Compartment 1:

|  | Example 11 | Example 12 | Example 13 |
|---|---|---|---|
| Volume (l) | 0.062 | 0.062 | 0.062 |
| Glucose (g/l) | 500 | 500 | 500 |
| $Na^+$ (mM) | 114.5 | 114.5 | 95.0 |
| $Ca^{2+}$ (mM) | 0.0 | 11.0 | 11.0 |
| $Cl^-$ (mM) | 92.0 | 120.0 | 117.0 |
| Citrate | 7.5 | 7.5 | 0.0 |

Compartment 2:

|  | Example 11 | Example 12 | Example 13 |
|---|---|---|---|
| Volume (l) | 0.103 | 0.103 | 0.103 |
| Glucose (g/l) | 500 | 500 | 500 |
| $Na^+$ (mM) | 114.5 | 114.5 | 95.0 |
| $Ca^{2+}$ (mM) | 0.0 | 14.0 | 14.0 |
| $Cl^-$ (mM) | 92.0 | 120.0 | 123.0 |
| Citrate (mM) | 7.5 | 7.5 | 0.0 |

Compartment 3:

|  | Example 11 | Example 12 | Example 13 |
|---|---|---|---|
| Volume (l) | 1.96 | 1.96 | 1.96 |
| $Na^+$ (mM) | 132.7 | 132.7 | 133.5 |
| $Cl^-$ (mM) | 95.4 | 94.7 | 97.7 |
| Citrate (mM) | 7.5 | 7.5 | 7.7 |
| Bicarbonate (mM) | 9.1 | 9.1 | 7.7 |
| Lactate (mM) | 9.1 | 9.1 | 7.7 |
| $Ca^{2+}$ (mM) | 1.42 | 1.1 | 1.1 |
| $Mg^{2+}$ (mM) | 0.27 | 0.27 | 0.27 |

Solution, mixed and ready for use:

|  | 1 + 3 | 2 + 3 | 1 + 2 + 3 |
|---|---|---|---|
| Example 11 |  |  |  |
| Volume (l) | 2.022 | 2.063 | 2.125 |
| Glucose (g/l) | 15.33 | 24.96 | 38.82 |
| $Na^+$ (mM) | 132.1 | 131.8 | 130.6 |
| $Cl^-$ (mM) | 95.3 | 95.2 | 95.1 |
| Citrate (mM) | 7.5 | 7.5 | 7.5 |
| Bicarbonate (mM) | 8.8 | 8.6 | 8.4 |
| Lactate (mM) | 8.8 | 8.6 | 8.4 |
| $Mg^{2+}$ (mM) | 0.26 | 0.25 | 0.25 |
| $Ca^{2+}$ (mM) | 1.38 | 1.35 | 1.31 |
| Example 12 |  |  |  |
| Volume (l) | 2.022 | 2.063 | 2.125 |
| Glucose (g/l) | 15.3 | 25.0 | 38.8 |
| $Na^+$ (mM) | 132.1 | 131.8 | 130.6 |
| $Cl^-$ (mM) | 95.3 | 96.0 | 96.5 |
| Citrate (mM) | 7.5 | 7.5 | 7.5 |
| Bicarbonate (mM) | 8.8 | 8.6 | 8.4 |
| Lactate (mM) | 8.8 | 8.6 | 8.4 |
| $Mg^{2+}$ (mM) | 0.26 | 0.25 | 0.25 |
| $Ca^{2+}$ (mM) | 1.40 | 1.74 | 2.01 |
| Example 13 |  |  |  |
| Volume (l) | 2.022 | 2.063 | 2.125 |
| Glucose (g/l) | 15.33 | 24.96 | 38.82 |
| $Na^+$ (mM) | 132.3 | 131.6 | 130.5 |
| $Cl^-$ (mM) | 98.3 | 99.0 | 99.5 |
| Citrate (mM) | 7.5 | 7.3 | 7.1 |
| Bicarbonate (mM) | 7.5 | 7.3 | 7.1 |
| Lactate (mM) | 7.5 | 7.3 | 7.1 |
| $Mg^{2+}$ (mM) | 0.26 | 0.25 | 0.25 |
| $Ca^{2+}$ (mM) | 1.40 | 1.74 | 2.01 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A peritoneal dialysis fluid comprising sodium ions, an osmotic agent, and a buffer, the peritoneal dialysis fluid further including citrate at a concentration of 4 to 10 mM in a final solution, said final solution being ready for use.

2. The peritoneal dialysis fluid according to claim 1, wherein the citrate is present at a concentration of 5-9 mM in the final solution.

3. The peritoneal dialysis fluid according to claim 1, wherein the citrate is present at a concentration of 7-8 mM in the final solution.

4. The peritoneal dialysis fluid according to claim 1, wherein the peritoneal dialysis fluid includes 1-10% by weight of the osmotic agent, 90-140 mM sodium ions, and 0.0-1.75 mM calcium ions in the final solution.

5. The peritoneal dialysis fluid according to claim 1, wherein the osmotic agent is selected from the group consisting of glucose, polymers of glucose, amino sugars, essential and non-essential amino acids, and N-acetyl glucose amine (NAG).

6. The peritoneal dialysis fluid according to claim 1, wherein the peritoneal dialysis fluid includes, as a buffer, bicarbonate, lactate, or bicarbonate and lactate in a total concentration of 5-28 mM in the final solution.

7. The peritoneal dialysis fluid according to claim 1, including 1.5-4% by weight of glucose as the osmotic agent in the final solution.

8. The peritoneal dialysis fluid according to claim 1, including 5-10% by weight of glucose polymer as the osmotic agent in the final solution.

9. The peritoneal dialysis fluid according to claim 1, including 1.5-4% by weight of N-acetyl glucose amine (NAG) as the osmotic agent in the final solution.

\* \* \* \* \*

UNITED STATES PATENT AND TRADEMARK OFFICE
CERTIFICATE OF CORRECTION

PATENT NO.       : 8,367,731 B2
APPLICATION NO.  : 11/921224
DATED            : February 5, 2013
INVENTOR(S)      : Wieslander et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1413 days.

Signed and Sealed this

First Day of September, 2015

Michelle K. Lee
*Director of the United States Patent and Trademark Office*